(12) United States Patent
Kamiya et al.

(10) Patent No.: US 8,334,321 B2
(45) Date of Patent: Dec. 18, 2012

(54) PROSTAGLANDIN FAT EMULSION, METHOD FOR PRODUCING THE SAME, METHOD FOR STABILIZING THE SAME, AND EMULSIFYING AGENT

(75) Inventors: Satomi Kamiya, Tokyo (JP); Tomonori Uchida, Tokyo (JP); Hideto Yoshida, Tokyo (JP); Yasutaka Inoue, Tokyo (JP); Noboru Yamada, Hyogo (JP); Kenichi Kajihara, Osaka (JP)

(73) Assignee: Q.P. Corporation (JP)

( * ) Notice: Subject to any disclaimer, the term of this patent is extended or adjusted under 35 U.S.C. 154(b) by 522 days.

(21) Appl. No.: 12/310,743

(22) PCT Filed: Sep. 3, 2007

(86) PCT No.: PCT/JP2007/067133
§ 371 (c)(1),
(2), (4) Date: Jan. 5, 2010

(87) PCT Pub. No.: WO2008/029763
PCT Pub. Date: Mar. 13, 2008

(65) Prior Publication Data
US 2010/0112066 A1 May 6, 2010

(30) Foreign Application Priority Data
Sep. 5, 2006 (JP) .................................. 2006-240572

(51) Int. Cl.
*A61K 31/5575* (2006.01)
*A61K 9/00* (2006.01)
*A61K 9/127* (2006.01)
*A61K 47/44* (2006.01)
*A61P 1/00* (2006.01)
*A61P 9/00* (2006.01)

(52) U.S. Cl. ........ 514/573; 424/400; 424/450; 514/937; 514/970

(58) Field of Classification Search .......................... None
See application file for complete search history.

(56) References Cited

U.S. PATENT DOCUMENTS

| | | | |
|---|---|---|---|
| 4,235,871 A * | 11/1980 | Papahadjopoulos et al. | 424/450 |
| 4,493,847 A | 1/1985 | Mizushima et al. | |
| 4,684,633 A | 8/1987 | Imagawa et al. | |
| 4,849,451 A | 7/1989 | Mizushima et al. | |
| 5,082,664 A * | 1/1992 | Lenk et al. | 424/450 |
| 5,120,870 A | 6/1992 | Mizushima et al. | |
| 5,194,670 A | 3/1993 | Mizushima et al. | |
| 6,214,375 B1 | 4/2001 | Modi | |
| 2003/0211140 A1 * | 11/2003 | Mantripragada et al. | 424/450 |
| 2004/0253276 A1 | 12/2004 | Sato et al. | |
| 2006/0134145 A1 | 6/2006 | Matsuda et al. | |

FOREIGN PATENT DOCUMENTS

| | | |
|---|---|---|
| JP | 58-222014 | 12/1983 |
| JP | 59-216820 | 12/1984 |
| JP | 60-149524 B1 | 8/1985 |
| JP | 03-204853 | 9/1991 |
| JP | 04-338333 | 11/1992 |
| JP | 04-356417 | 12/1992 |
| JP | 05-139977 | 6/1993 |
| JP | 07-069878 | 3/1995 |
| JP | 2001-010958 | 1/2001 |
| JP | 2003-501376 A | 1/2003 |
| JP | 2005-500366 | 1/2005 |
| TW | 181889 | 4/1992 |
| WO | WO 92/04886 | 4/1992 |
| WO | WO 9622764 A1 * | 8/1996 |
| WO | WO 00/74653 A1 | 12/2000 |
| WO | WO 03/013513 | 2/2003 |
| WO | WO 2004/032980 A1 | 4/2004 |
| WO | WO 2004/052354 | 6/2004 |

OTHER PUBLICATIONS

Ken-ichirou Akashi, Hidetake Miyata, Hiroyasu Itoh, & Kazuhiko Kinosita, Jr.; "Formation of Giant Liposomes Promoted by Divalent Cations: Critical Role of Electrostatic Repulsion" Biophysical Journal, vol. 74, Jun. 1998, pp. 2973-2982.*
"Egg Yolk Lecithin PC-98N", Kewpie corporation, 2011.*
Scholfield, C.R. "Composition of Soybean Lecithin", JAOCS, Oct. 1981, p. 889-892.*
"Introduction to the Use of Lecithins", Solae Company, 2012, pp. 1-11.*
International Search Report, from PCT/JP2007/067133, mailed Nov. 6, 2007.
Australian Search Report and Written Opinion, from SG 200900916-8, mailed Aug. 24, 2009.
English translation of Chinese Office Action for Application No. 2007-80032742.0 mailed Jul. 21, 2010 (7 pages).
Australian Patent Office Examination Report for Application No. SG 2009-00916-8 dated Jun. 3, 2010 (4 pages).
Supplementary European Search Report for Application No. EP 07 80 6606 dated May 27, 2011 (2 pages).
English translation of International Preliminary Report on Patentability for Application No. PCT/JP2007/067133 dated Mar. 17, 2009 (6 pages).
Partial Translation of Office Action dated Jun. 12, 2012, for Russian Patent Application No. 2009112547.

* cited by examiner

*Primary Examiner* — Ernst Arnold
*Assistant Examiner* — Christopher R Lea
(74) *Attorney, Agent, or Firm* — Harness, Dickey & Pierce, P.L.C.

(57) ABSTRACT

A fat emulsion comprises a prostaglandin as an active ingredient, the fat emulsion comprising a phospholipid that comprises phosphatidylcholine (PC) and phosphatidylglycerol (PG) and has a ratio of PC to PG (PC:PG) of 85:15 to 99.7:0.3.

22 Claims, No Drawings

US 8,334,321 B2

PROSTAGLANDIN FAT EMULSION, METHOD FOR PRODUCING THE SAME, METHOD FOR STABILIZING THE SAME, AND EMULSIFYING AGENT

TECHNICAL FIELD

The present invention relates to a prostaglandin fat emulsion that exhibits excellent stability of active ingredient and excellent emulsion stability, a method of producing the prostaglandin fat emulsion, a method of stabilizing the prostaglandin fat emulsion, and an emulsifying agent used for the stabilization method.

BACKGROUND ART

A prostaglandin is a physiologically active substance that is synthesized from an essential fatty acid having 3 to 5 double bonds. The prostaglandin is involved in adjustments of inflammation, pain, and swelling, adjustments of a blood pressure function, a cardiac function, and a gastrointestinal function, adjustments of a digestive enzyme secretion, adjustments of a renal function, blood coagulation, platelet aggregation, an allergic reaction, neural transmission, production of various hormones, and the like.

As a prostaglandin E1 (PGE1) preparation, intravenous-injection fat emulsions have been developed (see JP-B-1-57094, JP-B-1-57096, and JP-A-2001-10958, for example). Some of these emulsions are commercially available.

However, commercially available PGE1 fat emulsions must be stored at a low temperature (e.g., 5° C. or less) while blocking light. The quality assurance period of such PGE1 fat emulsions is short (e.g., 5° C.×1 year) even if the PGE1 fat emulsions are stored at a low temperature. This is because PGE1 (active ingredient) is chemically unstable. For example, since PGE1 fat emulsions must be prevented from freezing during storage, strict temperature control is necessary when storing PGE1 fat emulsions at 5° C. Since commercially available PGE1 fat emulsions must be stored under strict temperature control, it is difficult to control the quality of PGE1 fat emulsions during storage. Various attempts have been made to improve the stability of PGE1 (see JP-B-8-18989 and JP-A-4-338333, for example). However, these attempts have failed in achieving a sufficient effect. Some documents disclose measures to improve the stability of fat emulsions (see JP-T-2005-500366 and WO2004/52354, for example). However, these documents are silent about prostaglandin fat emulsions.

In view of this situation, development of a prostaglandin fat emulsion that exhibits excellent stability of active ingredient (prostaglandin) and excellent emulsion stability has been desired.

DISCLOSURE OF THE INVENTION

The invention provides a prostaglandin fat emulsion that comprises a prostaglandin as an active ingredient and exhibits excellent stability of active ingredient and excellent emulsion stability, a method of producing the prostaglandin fat emulsion, a method of stabilizing the prostaglandin fat emulsion, and an emulsifying agent used for the stabilization method.

A fat emulsion according to one aspect of the invention comprises a prostaglandin as an active ingredient, the fat emulsion comprising a phospholipid that comprises phosphatidylcholine (PC) and phosphatidylglycerol (PG) and has a ratio of PC to PG (PC:PG) of 85:15 to 99.7:0.3.

In the above fat emulsion, the ratio of PC to PG (PC:PG) may be 95:5 to 99.7:0.3. In this case, the ratio of PC to PG (PC:PG) may be 97:3 to 99.5:0.5.

The above fat emulsion may not substantially comprise phosphatidylethanolamine (PE).

In the above fat emulsion, the PG may comprise a linear saturated or unsaturated fatty acid residue having 12 to 18 carbon atoms.

In the above fat emulsion, the PG may be derived from egg yolk.

The above fat emulsion may not substantially comprise a free higher fatty acid or its salt.

The above fat emulsion may not substantially comprise free oleic acid.

The above fat emulsion may comprise a free higher fatty acid or its salt in an amount of 0.015 parts or less by mass with respect to 1 part by mass of the phospholipid. The above fat emulsion may comprise a free higher fatty acid or its salt in an amount of 0.15 parts or less by mass with respect to 1 part by mass of the phospholipid. In this case, the free higher fatty acid may be free oleic acid.

In the above fat emulsion, the total content of the PC and the PG in the phospholipid may be 95% or more.

The above fat emulsion may be used for intravenous injection.

In the above fat emulsion, the prostaglandin may be prostaglandin E1 or its derivative.

In the above fat emulsion, the prostaglandin may be prostaglandin E1.

In this case, the fat emulsion may have an average particle diameter of 300 nm or less and a prostaglandin E1 residual rate after storage at 40° C. for seven days of 70% or more.

The fat emulsion may have an average particle diameter of 300 nm or less and a prostaglandin E1 residual rate after storage at 40° C. for seven days of 80% or more.

The fat emulsion may have an average particle diameter of 300 nm or less and a prostaglandin E1 residual rate after storage at 40° C. for seven days of 85% or more.

The fat emulsion may have an average particle diameter of 300 nm or less and a prostaglandin E1 residual rate after storage at 20° C. for two months of 80% or more.

The fat emulsion may have an average particle diameter of 300 nm or less and a prostaglandin E1 residual rate after storage at 5° C. for one year of 80% or more.

A method of producing a fat emulsion according to one aspect of the invention comprises preparing a fat emulsion that comprises a prostaglandin as an active ingredient comprising a phospholipid that comprises phosphatidylcholine (PC) and phosphatidylglycerol (PG) and has a ratio of PC to PG (PC:PG) of 85:15 to 99.7:0.3.

In the above method of producing a fat emulsion, the pH of the fat emulsion may be adjusted to 4 to 7.

In the above method of producing a fat emulsion, the pH of the fat emulsion may be adjusted to 4.5 to 6.5.

A method of stabilizing a prostaglandin according to one aspect of the invention comprises using a phospholipid that has a ratio of phosphatidylcholine (PC) to phosphatidylglycerol (PG) (PC:PG) of 85:15 to 99.7:0.3 and substantially does not comprise phosphatidylethanolamine (PE) in a fat emulsion that comprises a prostaglandin as an active ingredient.

A method of stabilizing fat globules according to one aspect of the invention comprises using a phospholipid that has a ratio of phosphatidylcholine (PC) to phosphatidylglycerol (PG) (PC:PG) of 85:15 to 99.7:0.3 and substantially does not comprise phosphatidylethanolamine (PE) in a fat emulsion that comprises a prostaglandin as an active ingredient.

An emulsifying agent according to a further aspect of the invention comprises a phospholipid that has a ratio of phosphatidylcholine (PC) to phosphatidylglycerol (PG) (PC:PG) of 85:15 to 99.7:0.3 and substantially does not comprise phosphatidylethanolamine (PE), the emulsifying agent being used for a fat emulsion that comprises a prostaglandin as an active ingredient.

Since the above fat emulsion comprises the phospholipid that comprises phosphatidylcholine (PC) and phosphatidylglycerol (PG) and has a ratio of PC to PG (PC:PG) of 85:15 to 99.7:0.3, the fat emulsion exhibits excellent stability of active ingredient (prostaglandin) and excellent emulsion stability. Therefore, the storage period can be extended and/or the storage temperature range can be increased as compared with a commercially available prostaglandin fat emulsion. For example, the quality assurance period (5° C.×1 year) of the PGE1 fat emulsion may be extended to about two years, or the storage temperature range may be increased to about 10° C. (see the results of the examples described later). This facilitates quality control during storage. Since the fat globules contained in the above fat emulsion have a small and uniform particle diameter, the medicine can be efficiently accumulated in the lesion site. Therefore, the fat emulsion exhibits an excellent efficiency even if the amount of administration is small.

BEST MODE FOR CARRYING OUT THE INVENTION

A fat emulsion that includes prostaglandin as an active ingredient (hereinafter may be referred to as "prostaglandin fat emulsion" or "fat emulsion") according to one embodiment of the invention, a method of producing the same, a method of stabilizing the same, and an emulsifying agent used for the stabilization method are described below. In the following embodiments, "%" indicates "mass %", and "part(s)" indicates "part(s) by mass".

1. Fat Emulsion

The prostaglandin fat emulsion according to this embodiment is an emulsified product (oil-in-water emulsion) that includes a prostaglandin (active ingredient), a phospholipid (emulsifying agent), base oil, and water. Specifically, the prostaglandin fat emulsion according to this embodiment is an emulsified product in which fat globules are dispersed in water. In each fat globule, the prostaglandin and the base oil are mainly included in a membrane that contains the phospholipid.

The content of each component in the prostaglandin fat emulsion according to this embodiment is as follows. Specifically, the content of the prostaglandin is 0.2 to 100 micrograms/ml, the content of the base oil is 5 to 50% with respect to the total amount of the fat emulsion, and the content of the phospholipid is 1 to 50% with respect to the amount of the base oil.

The prostaglandin fat emulsion according to this embodiment may further include a higher fatty acid, an isotonizing agent, an antioxidant, and a pH adjusting agent, if necessary.

The pH of the fat emulsion according to this embodiment is preferably 4 to 7, and more preferably 4.5 to 6.5. If the pH of the fat emulsion according to this embodiment is less than 4, the emulsion stability may decrease. If the pH of the fat emulsion is more than 7, the stability of the active ingredient may decrease.

Each component of the fat emulsion according to this embodiment is described below.

1.1. Prostaglandin

The term "prostaglandin" is a generic name for compounds having prostanoic acid as the basic skeleton. The prostaglandin is classified into A, B, C, D, E, F, G, H, I, and the like corresponding to the ring structure. The prostaglandin is a physiologically active substance that functions as a cell signaling substance relating to smooth muscle stimulation, inflammation, allergy, secretion/aggregation/swarming of cells, cell growth, neural transmission, and the like. Specifically, the prostaglandin has a physiological activity such as a smooth muscle contracting activity (e.g., uterine muscle and isolated small intestine), a hypotensive activity, a vasopressor activity, an antilipolytic activity, a gastric secretion inhibition activity, an activity on the central nervous system, a platelet adhesion decreasing activity, a platelet aggregation inhibition activity, a thrombogenesis inhibition activity, an epidermal growth activity, and a keratinization stimulation activity depending on the type of prostaglandin.

Examples of the prostaglandin included in the fat emulsion according to this embodiment include PGA1, PGB1, PGD2, PGE1, PGE2, PGF1alpha, PGF2alpha, PGI2, and derivatives thereof. Among these, PGE1 and its derivatives are preferable. An alkyl ester is preferable as the prostaglandin derivative (see Japanese Patent No. 2602964, for example).

For example, PGE1 has a vasodilation activity, an antihypertensive activity, a renal blood flow increasing activity, a natriuresis activity, a renin secretagogue activity, an erythropoietin secretagogue activity, a platelet aggregation inhibition activity, a bronchodilator activity, a uterine contraction activity, an intestine movement acceleration activity, a stomach/intestine longitudinal muscle contraction activity, a stomach/intestine ring-shaped muscle relaxation activity, a gastric secretory inhibition activity, a gastric mucosal protection activity, an immunosuppression activity, an activity of suppressing norepinephrine release from peripheral sympathetic nerve endings, and the like. Therefore, the fat emulsion according to this embodiment that contains PGE1 may be used for treatment of an extremity ulcer and a rest pain due to chronic arterial occlusion, treatment of a skin ulcer due to progressive systemic sclerosis or diffuse lupus erythematosus, treatment of a skin ulcer due to diabetes, improvement of a rational symptom caused by peripheral vascular disease and recovery from a peripheral circulatory/nervous/motor disorder due to vibration, treatment of patent ductus arteriosus due to arterial canal-dependent congenital heart disease, and improvement in imaging capability in portography via superior mesenteric artery.

1.2. Phospholipid

The phospholipid used in the fat emulsion according to this embodiment includes phosphatidylcholine (PC) and phosphatidylglycerol (PG). The phospholipid may be a pharmaceutically acceptable salt such as a sodium salt, a potassium salt, or an ammonium salt.

Examples of PC include egg-yolk lecithin, soybean lecithin, lecithin synthesized or semi-synthesized by a known method, and the like. Among these, egg-yolk lecithin is preferable. In particular, purified egg-yolk lecithin having an increased phospholipid content, and highly purified egg-yolk lecithin that substantially does not contain PE, are preferable.

The term "purified egg-yolk lecithin" is defined in Japanese Pharmaceutical Excipients, and the term "highly purified egg-yolk lecithin" is defined in the Japanese Pharmaceutical Excipients Directory (edited by the Japan Pharmaceutical Excipients Council). Purified egg-yolk lecithin normally contains about 12 to 18% of PE.

It is preferable that the fat emulsion according to this embodiment substantially does not contain PE. A fat emulsion that substantially does not contain PE may be produced by utilizing highly purified egg-yolk lecithin or lecithin obtained by synthesis or semi-synthesis as the phospholipid.

Whether or not the phospholipid substantially does not contain PE may be checked by the following method, for example.

Specifically, the phospholipids is dissolved in a chloroform-methanol mixed solvent in an amount of 10% (w/v). The bottom of a silica gel thin-layer plate is charged with 10 microliters of the solution. The solution is developed using a developing solvent (chloroform:methanol:water=65:25:4), followed by drying. After spraying a ninhydrine reagent, the solution is heated at 120° C. for about ten minutes. When coloration is not observed in the spot area detected using a PE standard solution that is charged similarly, it is determined that the phospholipid substantially does not contain PE.

PG may be produced by chemical synthesis, may be extracted from a plant or bacteria, or may be prepared by causing a phospholipase D to act on lecithin derived from a soybean or egg yolk as a raw material in the presence of glycerol in accordance with a known method (Biochemistry Experiments 3, Lipid Chemistry, pages. 294 and 295, Tokyo Kagaku Dojin, 1974).

PG generally contains a linear or branched saturated or unsaturated fatty acid residue having 12 to 22 carbon atoms. In the fat emulsion according to this embodiment, PG preferably contains a linear saturated or unsaturated fatty acid residue having 12 to 18 carbon atoms, and more preferably a linear saturated or unsaturated fatty acid residue having 16 to 18 carbon atoms.

When using PG containing a fatty acid residue having carbon atoms in the above-mentioned range (particularly when using PC derived from egg-yolk lecithin), the chain length of the fatty acid of PC is almost equal to the chain length of the fatty acid of PG so that a more stabilized fat emulsion is obtained.

PG prepared by chemical synthesis may be at least one of dipalmitoylphosphatidylglycerol, dioleoylphosphatidylglycerol, dilauroylphosphatidylglycerol, dimyristoylphosphatidylglycerol, distearoylphosphatidylglycerol, and palmitoyloleoylphosphatidylglycerol. As a naturally-occurring PG, PG having a fatty acid residue specific to the substance from which PG is derived may be used. Among these, dipalmitoylphosphatidylglycerol, PG derived from soybean lecithin, or PG derived from egg-yolk lecithin is preferable, with PG derived from egg-yolk lecithin being more preferable from the viewpoint of the stability of the active ingredient and biocompatibility.

In the fat emulsion according to this embodiment, the ratio of PC to PG (PC:PG) in the phospholipid is 85:15 to 99.7:0.3. If the ratio of PC to PG (PC:PG) is within above-mentioned range, the stability of the active ingredient and the emulsion stability can be improved. If the amount of PG exceeds the above-mentioned range, the stability of PGE1 during storage is adversely affected. The ratio of PC to PG (PC:PG) is preferably 90:10 to 99.7:0.3, more preferably 95:5 to 99.7:0.3, and still more preferably 97:3 to 99.5:0.5.

In order to improve the chemical stability of the active ingredient, the total content of PC and PG in the phospholipid is preferably 95% or more, and more preferably 98% or more.

The phospholipid may include a phospholipid other than PC and PG (e.g., at least one of sphingomyelin, phosphatidylinositol, phosphatidylpolyglycerol, phosphatidyl ethylene glycol, phosphatidyl polyethylene glycol, lysophospholipids of these compounds, lyso-PC, and lyso-PG) in an amount of less than 5%. The naturally-occurring phospholipid may include triglycerol, cholesterol, and the like in an amount of less than 5%.

1.3. Base Oil

Examples of the base oil used in the fat emulsion according to this embodiment include vegetable oil such as soybean oil, sesame oil, rapeseed oil, safflower oil, olive oil, castor oil, corn oil, cottonseed oil, rice oil, sunflower oil, grapeseed oil, and wheat germ oil, a medium-chain triglyceride (MCT), and the like. The vegetable oil is preferably purified vegetable oil.

1.4. Higher Fatty Acid

In the fat emulsion according to this embodiment, the free higher fatty acid has a function of an emulsification adjuvant. Specifically, the emulsion stability of the fat emulsion according to this embodiment can be improved by utilizing the free higher fatty acid. The term "free higher fatty acid" used herein refers to a carboxylic acid. The term "salt of the free higher fatty acid" used herein refers to a pharmaceutically acceptable salt (e.g., alkali metal salts such as a sodium salt and a potassium salt, and alkaline earth metal salts such as a calcium salt) of the free higher fatty acid. The term "free higher fatty acid or its salt" excludes a fatty acid ester that forms the vegetable oil (base oil) and the phospholipid. The free higher fatty acid or its salt included in the fat emulsion excludes a free higher fatty acid contained in the vegetable oil (base oil) and the phospholipid.

The higher fatty acid is a linear or branched saturated or unsaturated fatty acid having 6 to 22 (preferably 12 to 20) carbon atoms. Examples of the higher fatty acid include oleic acid, stearic acid, linoleic acid, palmitic acid, linolenic acid, and myristic acid. Among these, oleic acid is preferable.

Since the fat emulsion according to this embodiment has excellent stability of active ingredient and emulsion stability, the fat emulsion may not substantially contain the free higher fatty acid or its salt (e.g., free oleic acid). When the fat emulsion contains the higher fatty acid or its salt, the amount of the higher fatty acid or its salt is preferably 0.15 parts or less, and more preferably 0.015 parts or less, based on 1 part of the phospholipid. If the amount of the higher fatty acid is more than 0.15 parts based on 1 part of the phospholipid, the stability of the active ingredient may decrease. If the amount of the higher fatty acid is 0.015 parts or less based on 1 part of the phospholipid, excellent emulsion stability can be obtained while maintaining the stability of the active ingredient. The statement "substantially does not contain the free higher fatty acid" used herein means that the free higher fatty acid is not added intentionally, but excludes a free higher fatty acid produced by decomposition of the vegetable oil (base oil) or the phospholipid and a free higher fatty acid that is mixed unintentionally.

Whether or not the fat emulsion substantially does not contain free oleic acid may be checked by the following method, for example.

Specifically, 1 ml of ethanol, 0.5 ml of diethyl ether, and 0.5 ml of a petroleum ether are added to 1 ml of the fat emulsion. The mixture is then stirred. After centrifuging the mixture, the supernatant liquid is collected. The solvent is then evaporated using nitrogen. The resulting oil phase component is dissolved in a chloroform-methanol mixed solvent in an amount of 10% (w/v). The bottom of a silica gel thin-layer plate is charged with 2 microliters of the solution. The solution is developed using a developing solvent (chloroform:methanol:water=65:25:4), followed by drying. After spraying 50% (w/w) sulfuric acid, the solution is heated at about 120° C. for 30 minutes. When coloration is not observed in the spot area detected using an oleic acid standard solution that is charged similarly, it is determined that the fat emulsion substantially does not contain free oleic acid.

Since the fat emulsion according to this embodiment substantially does not contain PE and/or the free higher fatty acid (e.g., free oleic acid), the number of components contained in the fat emulsion can be reduced. Moreover, the stability of the active ingredient can be further improved.

1.5. Other Components

The fat emulsion according to this embodiment may include an isotonizing agent (e.g., glycerol, glucose, and sodium chloride), an antioxidant (e.g., ascorbic acid and its salts, benzoic acid, citric acid and its salts, dibutylhydroxyanisole, dibutylhydroxytoluene, alpha-tocopherol, and D-sorbitol), and a PH adjusting agent (e.g., sodium hydroxide, hydrochloric acid, and phosphate), if necessary.

1.6. Production Method

A method of producing a prostaglandin fat emulsion according to one embodiment of the invention includes preparing a fat emulsion using a phospholipid that includes phosphatidylcholine (PC) and phosphatidylglycerol (PG), the ratio of PC to PG (PC:PG) being 85:15 to 99.7:0.3, preferably 90:10 to 99.7:0.3, more preferably 95:5 to 99.7:0.3, and still more preferably 97:3 to 99.5:0.5. Specifically, the fat emulsion is prepared by emulsifying a prostaglandin (active ingredient), the phospholipid (emulsifying agent), base oil, and water.

PC and PG may be mixed into the base oil or water. After homogenizing the mixture, water or the base oil may be added to the mixture to prepare an emulsion. It is preferable to homogenize PC and PG in the base oil.

For example, the phospholipid (PC and PG), the prostaglandin (e.g., PGE1), additives (e.g., glycerol), and the like are mixed into a specific amount of base oil (e.g., soybean oil), and the mixture is homogenized using a homogenizer. After the addition of a specific amount of water, the mixture is homogenized using the homogenizer to obtain an oil-in-water emulsion. The fat emulsion according to this embodiment can thus be produced.

PC and PG may be added separately or simultaneously. PG obtained by partially converting PC into PG by an enzyme reaction may be used. A phospholipid obtained by adding an unpurified product or a purified product that contains PG or PC so that the ratio of PC to PG (PC:PG) is 85:15 to 99.7:0.3 in the purification process of PC or PG may be used. When using PC derived from egg yolk, PC in egg yolk may be converted into PG by an enzyme reaction to make egg yolk liquid so that the ratio of PC to PG (PC:PG) is 85:15 to 99.7:0.3. Then the phospholipid in the egg yolk liquid may be purified and used.

Additives such as a stabilizer, an isotonizing agent, and a pH adjusting agent may be added to the fat emulsion according to this embodiment for convenience of production. The resulting fat emulsion may be filtered or heated (e.g., high-temperature heat treatment).

The method of producing a prostaglandin fat emulsion according to this embodiment may further include adjusting the pH of the fat emulsion to preferably 4 to 7 (more preferably 4.5 to 6.5). If the pH of the fat emulsion according to this embodiment is less than 4, the emulsion stability may decrease. If the pH of the fat emulsion is more than 7, the stability of the active ingredient may decrease.

The method of producing a prostaglandin fat emulsion according to this embodiment may further include placing the fat emulsion of which the pH has been adjusted to 4 to 7 in an airtight container, and subjecting the fat emulsion to a high-temperature heat treatment at a specific temperature for a specific period of time. The fat emulsion can be sterilized by the high-temperature heat treatment while suppressing decomposition of the active ingredient (prostaglandin). The high-temperature heat treatment is preferably a high-pressure steam thermal sterilization treatment or a spray thermal sterilization treatment.

The high-pressure steam thermal sterilization treatment or the spray thermal sterilization treatment are preferably carried out at 110 to 140° C. for 0.5 to 30 minutes. For example, the high-pressure steam heat treatment may be carried out at 127° C. for one minute. The conditions of 127° C. for one minute correspond to a $F_0$ value of about 9 to 10 that is an example of microorganism killing heating conditions.

The fat emulsion obtained by the above-mentioned production process exhibits excellent emulsion stability and excellent active ingredient (prostaglandin) stability. For example, the fat emulsion that has been subjected to the high-temperature heat treatment has a prostaglandin residual rate of 70% or more, preferably 80% or more, and more preferably 85% or more, with respect to the fat emulsion that is not subjected to the high-temperature heat treatment.

1.7. Stabilization Method and Emulsifying Agent

A method of stabilizing a prostaglandin fat emulsion according to one embodiment of the invention includes using a phospholipid that has a ratio of PC to PG (PC:PG) of 85:15 to 99.7:0.3 and substantially does not contain PE in a fat emulsion that includes a prostaglandin as an active ingredient. An emulsifying agent according to one embodiment of the invention is used for a prostaglandin fat emulsion, the emulsifying agent including a phospholipid that has a ratio of PC to PG (PC:PG) of 85:15 to 99.7:0.3 and substantially does not contain PE. Examples of such an emulsifying agent include the above-mentioned highly purified egg-yolk lecithin that contains PC and PG in the above-mentioned ratio.

1.8. Application and Properties

Since the fat emulsion according to this embodiment includes the phospholipid that includes phosphatidylcholine (PC) and phosphatidylglycerol (PG) and has a ratio of PC to PG (PC:PG) of 85:15 to 99.7:0.3, the stability of the active ingredient (prostaglandin) can be improved while maintaining the emulsion stability even if the fat emulsion substantially does not contain a free fatty acid such as oleic acid. Since the fat emulsion according to this embodiment substantially does not contain PE, the stability of the active ingredient (prostaglandin) can be further improved.

The fat emulsion according to this embodiment may be used for intravenous injection. In this case, after adjusting the pH of the fat emulsion obtained according to this embodiment, an airtight container such as an ampule, a vial, or a prefilled syringe container is charged with the fat emulsion. The fat emulsion may then be subjected to a high-temperature heat treatment or the like.

The average diameter of the fat emulsion according to this embodiment is preferably 300 nm or less, and more preferably 150 to 250 nm. If the average diameter is larger than 300 nm, the emulsion system of the fat emulsion may become unstable. If the average diameter is smaller than 150 nm, the rate of accumulation in the inflammation site (particularly the peripheral vessel inner wall) or macrophages decreases when the fat emulsion is administered intravenously. As a result, the fat emulsion may exhibit insufficient physiological activities after administration.

The fat emulsion according to this embodiment preferably has an average diameter of 300 nm or less, the prostaglandin is preferably PGE1, and the fat emulsion preferably has a PGE1 residual rate after storage at 40° C. for seven days of 70% or more, preferably 80% or more, and more preferably 85% or more. The fat emulsion preferably has a prostaglandin E1 residual rate after storage at 20° C. for two months of 70% or more, preferably 80% or more, and more preferably 85% or more. The fat emulsion preferably has a prostaglandin E1 residual rate after storage at 5° C. for one year of 80% or more, preferably 85% or more, and more preferably 90% or more. In the invention, the storage test at 40° C. for seven days is a test for evaluating the long-term storage stability of the fat emulsion (see JP-A-4-338333, for example). The storage test at 20° C. for two months is a test for evaluating the long-term storage stability of the fat emulsion according to this embodiment (see ICH guideline Q1A, for example).

Since the fat emulsion according to this embodiment includes the phospholipid that includes PC and PG and has a ratio of PC to PG (PC:PG) of 85:15 to 99.7:0.3, the fat emulsion has excellent stability of PGE1 (active ingredient) without making it necessary to limit other additives added to the fat emulsion, or increase the average diameter of the fat globules contained in the fat emulsion, or causing a variation in the particle size distribution of the fat globules contained in the fat emulsion. Since the fat globules contained in the fat emulsion according to this embodiment have a small and uniform particle diameter like a conventional art, the medicine is efficiently accumulated in the lesion site. Therefore, the fat emulsion exhibits an excellent efficiency even if the amount of administration is small.

The PGE1 residual rate (%) in the fat emulsion after storage is calculated by the following expression (1) based on the PGE1 content in the fat emulsion immediately after the high-temperature heat treatment and the PGE1 content in the fat emulsion after storage was quantitated by high performance liquid chromatography (HPLC). The details of the method of quantitating the PGE1 content in the fat emulsion by HPLC are given in the examples described later.

PGE1 residual rate (%)=(PGE1 content (g) in fat emulsion after storage/PGE1 content (g) in fat emulsion immediately after high-temperature heat treatment)×100     (1)

1.9. Dosage Form

The fat emulsion according to this embodiment is preferably administered to a human or a mammal other than a human by a parenteral administration route. It is more preferable that the fat emulsion be administered by, intravenous injection (including intravenous drip injection). For example, the fat emulsion according to this embodiment that contains 0.2 to 100 micrograms/ml of the prostaglandin may be administered by intravenous injection either directly or after being mixed into an infusion solution.

2. EXAMPLES

The invention is further described below by way of examples. Note that the invention is not limited to the following examples.

2.1. Evaluation Method

In the examples, the PGE1 content in the fat emulsion was quantitated by the following methods and the average diameter of the fat globules contained in the fat emulsion was measured by the following methods.

2.1.1. PGE1 Content

The fat emulsion was pretreated using an SEP-PAKC$_{18}$ cartridge (manufactured by Waters), and the PGE1 content in the fat emulsion was quantitated by HPLC using a post-column method. The operational conditions were as follows.
Detector: ultraviolet absorptiometer (measurement wavelength: 278 nm)
Column: octadecylsilylated silica gel (inner diameter: 4 mm, length: 15 cm)
Column temperature: about 60° C.
Mobile phase: 1/150 mol/l phosphate buffer-acetonitrile mixture (3:1) (pH: 6.3)
Flow rate of mobile phase: 1 ml/min
(Post-Column Reaction Conditions)
Reaction liquid: 1 mol/l potassium hydroxide solution
Flow rate: 0.5 ml/min
Reaction coil: Teflon (trade name) tube (inner diameter: about 0.5 mm, length: about 10 m)
Reaction temperature: about 60° C.

2.1.2. Average Diameter of Fat Globules

The average diameter of the fat globules contained in the fat emulsion was measured using an N4PLUS submicron particle size distribution measurement device (manufactured by Beckman Coulter, Inc.).

2.1.3. Detection of PE in Fat Emulsion 1 ml of ethanol, 0.5 ml of diethyl ether, and 0.5 ml of a petroleum ether were added to 1 ml of the fat emulsion. The mixture was then stirred. After centrifuging the mixture, the supernatant liquid was collected. The solvent was then evaporated using nitrogen. The resulting oil phase component was dissolved in a chloroform-methanol mixed solvent in an amount of 10% (w/v). The bottom of a silica gel thin-layer plate was charged with 20 microliters of the solution. The solution was developed using a developing solvent (chloroform:methanol:water=65:25:4), followed by drying. After spraying a ninhydrine reagent, the solution was heated at about 120° C. for ten minutes. When coloration was not observed in the spot area detected using a PE standard solution that was charged similarly, it was determined that the fat emulsion substantially did not contain PE.

2.2. Example 1

50 g of soybean oil (base oil), 8.82 g of egg-yolk lecithin "PC-98N" (manufactured by Q.P. Corporation, phosphatidylcholine purity: 98.8%, PE was not detected by the above-mentioned phospholipid PE detection method) (phospholipid), and 0.18 g of dipalmitoylphosphatidylglycerol (manufactured by NOF Corporation) were dispersed and homogenized using a homomixer. After the addition of 3.5 mg of prostaglandin E1, water for injection in which 11.05 g of concentrated glycerin (specified in the Japanese Pharmacopoeia) was dissolved was added to the mixture to obtain 500 g of a coarse emulsified liquid. The coarse emulsified liquid was caused to pass through a Manton-Gaulin homogenizer (manufactured by APV) fifteen times at a pressure of 600 kgf/cm$^2$ to obtain a fat emulsion of Example 1 (average particle diameter: 193 nm and 213 nm). The average particle diameter of the fat globules contained in the fat emulsion was measured, and the PGE1 content in the fat emulsion was quantitated.

The PGE1 content in the fat emulsion (the PGE1 content in the fat emulsion immediately after preparation) is shown in Tables 1 and 2, and the average particle diameter of the fat globules contained in the fat emulsion (the average particle diameter of the fat globules contained in the fat emulsion immediately after preparation) is shown in Tables 3 and 4.

The fat emulsion was filtered through a membrane filter having a pore diameter of 0.45 micrometers. The pH of the fat emulsion was then adjusted to 5.0, 5.5 (two samples), or 6.0 using a sodium hydroxide aqueous solution. After pipetting the fat emulsion into a 2 ml ampule, the fat emulsion was subjected to a spray thermal sterilization treatment (i.e., high-temperature heat treatment) at 110° C. for five minutes. After opening the ampule, the residual rate of PGE1 in the fat emulsion (the residual rate of PGE1 in the fat emulsion immediately after heating) was calculated, and the average particle diameter of the fat globules contained in the fat emulsion (the average particle diameter of the fat globules contained in the fat emulsion immediately after heating) was measured. The results are shown in Tables 1 to 4.

The residual rate of PGE1 in the fat emulsion immediately after heating was calculated by quantitating the PGE1 content in the fat emulsion immediately after the high-temperature heat treatment according to the above-described PGE1 content quantitating method, and calculating the ratio (%) of the PGE1 content in the fat emulsion immediately after the high-temperature heat treatment to the PGE1 content in the fat emulsion immediately after preparation.

The ampule subjected to the high-temperature heat treatment was stored at 40° C. for seven days. After opening the ampule, the PGE1 content in the fat emulsion after storage at 40° C. for seven days was quantitated. The residual rate of PGE1 in the fat emulsion after storage at 40° C. for seven days was calculated based on the expression (1). The average particle diameter of the fat globules contained in the fat emulsion after storage at 40° C. for seven days was also measured. The results are shown in Tables 1 to 4. PE was not detected in the fat emulsion of Example 1.

Examples 1, 2, and 4 to 6 and Comparative Examples 2, 3, and 6 indicate the results when the pH was adjusted to 5.0, Examples 1, 2, 4, 7, 9, 10, and 12 and Comparative Examples 1 to 4, 6, and 7 indicate the results when the pH was adjusted to 5.5, and Examples 1, 3, 7, 8, and 11 and Comparative Examples 3 and 5 indicate the results when the pH was adjusted to 6.0 (see Tables 1 to 4).

In Examples 1 to 12 and Comparative Examples 1 to 7, the amount of PC was calculated by multiplying the amount of phospholipid (egg-yolk lecithin) by the purity (0.988=98.8%) of PC.

In Tables 1 and 2, "oleic acid (parts by mass)" indicates the content (parts by mass) of oleic acid with respect to 1 part by mass of the phospholipid.

2.3. Example 2

A fat emulsion of Example 2 (average particle diameter: 222 nm) was obtained in the same manner as in Example 1, except that the amount of egg-yolk lecithin "PC-98N" was changed to 8.55 g and the amount of dipalmitoylphosphatidylglycerol was changed to 0.45 g. The pH of the fat emulsion was adjusted to 5.0 or 5.5 using dilute hydrochloric acid.

The fat emulsions of Example 2, Examples 3 to 12, and Comparative Examples 1 to 7 described later were subjected to the high-temperature heat treatment and stored at 40° C. for seven days in the same manner as in Example 1. The residual rate of PGE1 in each fat emulsion and the average particle diameter of the fat globules contained in each fat emulsion were measured. The results are shown in Tables 1 to 4. PE was not detected in the fat emulsion of Example 2.

2.4. Example 3

Reference Example

A fat emulsion of Example 3 (average particle diameter: 229 nm) was obtained in the same manner as in Example 1, except that the amount of egg-yolk lecithin "PC-98N" was changed to 7.65 g, 1.35 g of PG prepared by subjecting PC obtained by purifying an egg-yolk phospholipid to a phospholipase D treatment in the presence of glycerol (hereinafter referred to as "egg yolk-derived PG") was used instead of dipalmitoylphosphatidylglycerol, and the high-temperature heat treatment conditions were changed to 127° C. and one minute. Regarding the fatty acid residues in the egg yolk-derived PG, fatty acid residues having 16 carbon atoms accounted for 35%, and fatty acid residues having 18 carbon atoms accounted for 57%. The pH of the fat emulsion was adjusted to 6.0 using a sodium hydroxide aqueous solution. PE was not detected in the fat emulsion of Example 3. The fat emulsion of Example 3 had an active ingredient (PGE1) residual rate immediately after heating lower than those of the fat emulsions of Examples 8 and 11 described later, for example. Therefore, it is considered that an increase in the amount of PG adversely affects the stability of the active ingredient after heating.

2.5. Example 4

A fat emulsion of Example 4 (average particle diameter: 226 nm) was obtained in the same manner as in Example 1, except that 0.6 g of oleic acid was added to the soybean oil. The pH of the fat emulsion was adjusted to 5.0 using dilute hydrochloric acid, or adjusted to 5.5 using a sodium hydroxide aqueous solution. PE was not detected in the fat emulsion of Example 4.

2.6. Example 5

A fat emulsion of Example 5 (average particle diameter: 210 nm) was obtained in the same manner as in Example 1, except that 1.2 g of oleic acid was added to the soybean oil. The pH of the resulting fat emulsion was 5.0. PE was not detected in the fat emulsion of Example 5.

2.7. Example 6

A fat emulsion of Example 6 (average particle diameter: 230 nm) was obtained in the same manner as in Example 2, except that 1.2 g of oleic acid was added to the soybean oil. The pH of the fat emulsion was adjusted to 5.0 using dilute hydrochloric acid. PE was not detected in the fat emulsion of Example 6.

2.8. Example 7

A fat emulsion of Example 7 (average particle diameter: 218 nm) was obtained in the same manner as in Example 3, except that the amount of egg-yolk lecithin "PC-98N" was changed to 8.82 g, the amount of egg yolk-derived PG was changed to 0.18 g, and the high-temperature heat treatment conditions were changed to 110° C. and five minutes. The pH of the fat emulsion was adjusted to 5.5 using dilute hydrochloric acid, or adjusted to 6.0 using a sodium hydroxide aqueous solution. PE was not detected in the fat emulsion of Example 7.

2.9. Example 8

A fat emulsion of Example 8 (average particle diameter: 197 nm) was obtained in the same manner as in Example 3, except that the amount of egg-yolk lecithin "PC-98N" was changed to 8.91 g and the amount of egg yolk-derived PG was changed to 0.09 g. The pH of the fat emulsion was adjusted to 6.0 using a sodium hydroxide aqueous solution. PE was not detected in the fat emulsion of Example 8.

2.10. Example 9

A fat emulsion of Example 9 (average particle diameter: 217 nm) was obtained in the same manner as in Example 8, except that 0.12 g of oleic acid was added to the soybean oil. The pH of the fat emulsion was adjusted to 5.5 using a sodium hydroxide aqueous solution. PE was not detected in the fat emulsion of Example 9.

2.11. Example 10

A fat emulsion of Example 10 (average particle diameter: 198 nm) was obtained in the same manner as in Example 8, except that the amount of egg-yolk lecithin "PC-98N" was changed to 8.955 g and the amount of egg yolk-derived PG was changed to 0.045 g. The pH of the fat emulsion was adjusted to 5.5 using dilute hydrochloric acid. PE was not detected in the fat emulsion of Example 10.

2.12. Example 11

A fat emulsion of Example 11 (average particle diameter: 195 nm) was obtained in the same manner as in Example 8, except that the amount of egg-yolk lecithin "PC-98N" was changed to 8.973 g and the amount of egg yolk-derived PG was changed to 0.027 g. The pH of the fat emulsion was adjusted to 6.0 using a sodium hydroxide aqueous solution. PE was not detected in the fat emulsion of Example 11. Since the average particle diameter of the fat emulsion of Example 11 increased after heating by about 50 nm, it is considered that the thermal stability of the fat emulsion of Example 11 was inferior to some extent. However, separation of the oil phase was not observed, and the stability of the active ingredient (PGE1) was excellent.

2.13. Example 12

A fat emulsion of Example 12 (average particle diameter: 227 nm) was obtained in the same manner as in Example 2, except that PG prepared by subjecting a soybean phospholipid to a phospholipase D treatment in the presence of glycerol (hereinafter referred to as "soybean-derived PG") was used instead of dipalmitoylphosphatidylglycerol, and the high-temperature heat treatment conditions were changed to 127° C. and one minute. Regarding the fatty acid residues in the soybean-derived PG, fatty acid residues having 16 carbon atoms accounted for 14%, and fatty acid residues having 18 carbon atoms accounted for 78%. The pH of the fat emulsion was adjusted to 5.5 using dilute hydrochloric acid. PE was not detected in the fat emulsion of Example 12.

2.14. Comparative Example 1

A fat emulsion of Comparative Example 1 (average particle diameter: 214 nm) was obtained in the same manner as in Example 5, except that the amount of egg-yolk lecithin "PC-98N" was changed to 9.0 g and the amount of dipalmitoylphosphatidylglycerol was changed to 0 g. The pH of the fat emulsion was adjusted to 5.5 using a sodium hydroxide aqueous solution. PE was not detected in the fat emulsion of Comparative Example 1.

2.15. Comparative Example 2

A fat emulsion of Comparative Example 2 (average particle diameter: 189 nm) was obtained in the same manner as in Example 1, except that the amount of egg-yolk lecithin "PC-98N" was changed to 9.0 g and the amount of dipalmitoylphosphatidylglycerol was changed to 0 g. The pH of the fat emulsion was adjusted to 5.0 using dilute hydrochloric acid, or adjusted to 5.5 using a sodium hydroxide aqueous solution. PE was not detected in the fat emulsion of Comparative Example 2.

2.16. Comparative Example 3

A fat emulsion of Comparative Example 3 (average particle diameter: 216 nm) was obtained in the same manner as in Comparative Example 1, except that the high-temperature heat treatment conditions were changed to 127° C. and one minute. The pH of the fat emulsion was adjusted to 5.0 using dilute hydrochloric acid, or adjusted to 5.5 or 6.0 using a sodium hydroxide aqueous solution. PE was not detected in the fat emulsion of Comparative Example 3.

2.17. Comparative Example 4

A fat emulsion of Comparative Example 4 (average particle diameter: 221 nm) was obtained in the same manner as in Example 12, except that phosphatidylserine (PS) prepared by subjecting PC obtained by purifying an egg-yolk phospholipid to a phospholipase D treatment in the presence of L-serine ("egg yolk-derived PS") was used instead of the soybean-derived PG. The pH of the fat emulsion was adjusted to 5.5 using a sodium hydroxide aqueous solution. PE was not detected in the fat emulsion of Comparative Example 4.

2.18. Comparative Example 5

A fat emulsion of Comparative Example 5 (average particle diameter: 192 nm) was obtained in the same manner as in Example 8, except that the amount of egg-yolk lecithin "PC-98N" was changed to 8.991 g and the amount of egg yolk-derived PG was changed to 0.009 g. The pH of the fat emulsion was adjusted to 6.0 using a sodium hydroxide aqueous solution. PE was not detected in the fat emulsion of Comparative Example 5. Since the fat emulsion of Comparative Example 5 was separated after heating, determination of PGE1 and the storage test were not conducted.

2.19. Comparative Example 6

A fat emulsion of Comparative Example 6 (average particle diameter: 195 nm) was obtained in the same manner as in Comparative Example 1, except that the amount of egg-yolk lecithin "PC-98N" was changed to 7 g, and 2 g of egg-yolk lecithin "PL-100M" (manufactured by Q.P. Corporation, PE content: 15.8%) was added. The pH of the fat emulsion was adjusted to 5.0 using dilute hydrochloric acid, or adjusted to 5.5 using a sodium hydroxide aqueous solution. The PE content in the phospholipid was 3.5% (i.e., PE was detected in the fat emulsion of Comparative Example 6).

2.20. Comparative Example 7

A fat emulsion of Comparative Example 7 (average particle diameter: 238 nm) was obtained in the same manner as in Example 12, except that dipalmitoylphosphatidic acid was used instead of the soybean-derived PG. The pH of the fat emulsion was adjusted to 5.5 using a sodium hydroxide aqueous solution. PE was not detected in the fat emulsion of Comparative Example 7.

TABLE 1

| | Oleic acid (parts by mass) | PC:PG | pH | Immediately after preparation PGE1 (microgram/ml) (a) | Immediately after heating PGE1 (microgram/ml) (b) | Immediately after heating PGE1 residual rate (%) (b/a) | After storage at 40° C. for 7 days PGE1 (microgram/ml) (c) | After storage at 40° C. for 7 days PGE1 residual rate (%) (c/b) |
|---|---|---|---|---|---|---|---|---|
| Example 1 | 0 | 98:2 | 5.0 | 7.29 | 6.78 | 92.9 | 5.69 | 83.9 |
| | | | 5.5 | | 6.71 | 92.0 | 5.76 | 85.9 |
| | | | 5.5 | 5.69 | 5.37 | 94.3 | 4.68 | 87.2 |
| | | | 6.0 | | 5.31 | 93.2 | 4.68 | 88.3 |
| Example 2 | 0 | 95:5 | 5.0 | 6.12 | 5.88 | 96.1 | 4.77 | 81.2 |
| | | | 5.5 | | 5.88 | 96.1 | 4.99 | 85.1 |
| Example 3 | 0 | 85:15 | 6.0 | 6.60 | 4.08 | 61.9 | 2.91 | 71.3 |
| Example 4 | 0.067 | 98:2 | 5.0 | 6.35 | 5.75 | 90.6 | 4.76 | 82.7 |
| | | | 5.5 | | 5.75 | 90.6 | 4.72 | 82.0 |
| Example 5 | 0.133 | 98:2 | 5.0 | 7.57 | 6.76 | 89.3 | 5.09 | 75.3 |
| Example 6 | 0.133 | 95:5 | 5.0 | 6.94 | 6.30 | 90.8 | 4.47 | 71.0 |
| Example 7 | 0 | 98:2 | 5.5 | 6.64 | 6.13 | 92.3 | 5.55 | 90.5 |
| | | | 6.0 | | 6.02 | 90.6 | 5.58 | 92.7 |
| Example 8 | 0 | 99:1 | 6.0 | 7.02 | 5.90 | 84.0 | 5.32 | 90.2 |
| Example 9 | 0.0133 | 99:1 | 5.5 | 6.97 | 6.01 | 86.2 | 5.23 | 87.0 |
| Example 10 | 0 | 99.5:0.5 | 5.5 | 7.20 | 6.28 | 87.2 | 5.67 | 90.3 |
| Example 11 | 0 | 99.7:0.3 | 6.0 | 7.66 | 6.52 | 85.1 | 5.86 | 89.9 |
| Example 12 | 0 | 95:5 | 5.5 | 7.18 | 5.69 | 79.2 | 4.60 | 80.9 |

TABLE 2

| | Oleic acid (parts by mass) | PC:PG | pH | Immediately after preparation PGE1 (microgram/ml) (a) | Immediately after heating PGE1 (microgram/ml) (b) | Immediately after heating PGE1 residual rate (%) (b/a) | After storage at 40° C. for 7 days PGE1 (microgram/ml) (c) | After storage at 40° C. for 7 days PGE1 residual rate (%) (c/b) |
|---|---|---|---|---|---|---|---|---|
| Comparative Example 1 | 0.133 | 100:0 | 5.5 | 7.20 | 6.32 | 87.8 | 4.21 | 66.7 |
| Comparative Example 2 | 0 | 100:0 | 5.0 | 6.34 | 5.89 | 92.9 | 5.58 | 94.8 |
| | | | 5.5 | | 5.84 | 92.1 | 5.59 | 95.8 |
| Comparative Example 3 | 0.133 | 100:0 | 5.0 | 7.12 | 5.95 | 83.5 | 4.36 | 73.4 |
| | | | 5.5 | | 5.76 | 80.9 | 4.07 | 70.6 |
| | | | 6.0 | | 5.52 | 77.5 | 3.63 | 65.9 |
| Comparative Example 4 | 0 | (PC:PS = 95:5) | 5.5 | 6.11 | 4.74 | 77.6 | 2.56 | 54.0 |
| Comparative Example 5 | 0 | 99.9:0.1 | 6.0 | — | — | — | — | — |
| Comparative Example 6 | 0.133 | (PC:PE = 96.5:3.5) | 5.0 | 7.10 | 5.66 | 79.7 | 2.52 | 44.5 |
| | | | 5.5 | | 5.61 | 79.0 | 2.44 | 43.5 |
| Comparative Example 7 | 0 | (PC:PA = 95:5) | 5.5 | 6.93 | 4.93 | 71.3 | 3.00 | 60.7 |

TABLE 3

| | pH | Immediately after preparation Average particle diameter (nm) | Immediately after preparation Standard deviation (nm) | Immediately after heating Average particle diameter (nm) | Immediately after heating Standard deviation (nm) | After storage at 40° C. for 7 days Average particle diameter (nm) | After storage at 40° C. for 7 days Standard deviation (nm) |
|---|---|---|---|---|---|---|---|
| Example 1 | 5.0 | 193 | 86 | 211 | 82 | 200 | 66 |
| | 5.5 | | | 214 | 88 | 213 | 88 |
| | 5.5 | 213 | 32 | 211 | 63 | 212 | 72 |
| | 6.0 | | | 212 | 78 | 213 | 82 |
| Example 2 | 5.0 | 222 | 68 | 218 | 80 | 225 | 78 |
| | 5.5 | | | 219 | 55 | 220 | 85 |
| Example 3 | 6.0 | 229 | 56 | 226 | 70 | 230 | 74 |
| Example 4 | 5.0 | 226 | 86 | 225 | 88 | 229 | 50 |
| | 5.5 | | | 227 | 74 | 225 | 80 |
| Example 5 | 5.0 | 210 | 85 | 211 | 71 | 217 | 66 |
| Example 6 | 5.0 | 230 | 74 | 223 | 60 | 232 | 68 |
| Example 7 | 5.5 | 218 | 86 | 219 | 68 | 215 | 80 |
| | 6.0 | | | 221 | 73 | 213 | 78 |
| Example 8 | 6.0 | 197 | 81 | 198 | 60 | 196 | 82 |
| Example 9 | 5.5 | 217 | 77 | 221 | 71 | 211 | 74 |
| Example 10 | 5.5 | 198 | 58 | 191 | 56 | 181 | 64 |

TABLE 3-continued

|  | pH | Immediately after preparation | | Immediately after heating | | After storage at 40° C. for 7 days | |
|---|---|---|---|---|---|---|---|
|  |  | Average particle diameter (nm) | Standard deviation (nm) | Average particle diameter (nm) | Standard deviation (nm) | Average particle diameter (nm) | Standard deviation (nm) |
| Example 11 | 6.0 | 195 | 67 | 239 | 53 | 234 | 72 |
| Example 12 | 5.5 | 227 | 93 | 233 | 85 | 226 | 74 |

TABLE 4

|  | pH | Immediately after preparation | | Immediately after heating | | After storage at 40° C. for 7 days | |
|---|---|---|---|---|---|---|---|
|  |  | Average particle diameter (nm) | Standard deviation (nm) | Average particle diameter (nm) | Standard deviation (nm) | Average particle diameter (nm) | Standard deviation (nm) |
| Comparative Example 1 | 5.5 | 214 | 33 | 219 | 47 | 219 | 63 |
| Comparative Example 2 | 5.0 | 189 | 69 | 731 (Separation occurred after heating) | 315 | 423 | 195 |
|  | 5.5 |  |  | (Separation occurred after heating, and mesurement was impossible |  | 413 | 185 |
| Comparative Example 3 | 5.0 | 216 | 78 | 419 | 189 | 427 | 179 |
|  | 5.5 |  |  | 311 | 76 | 340 | 99 |
|  | 6.0 |  |  | 227 | 75 | 226 | 67 |
| Comparative Example 4 | 5.5 | 221 | 29 | 225 | 77 | 219 | 80 |
| Comparative Example 5 | 6.0 | 192 | 78 | 753 (Separation occurred after heating) | 354 | — | — |
| Comparative Example 6 | 5.0 | 195 | 70 | 191 | 76 | 197 | 72 |
|  | 5.5 |  |  | 187 | 68 | 186 | 71 |
| Comparative Example 7 | 5.5 | 238 | 53 | 239 | 65 | 238 | 66 |

In Tables 1 and 2, "PC:PG" indicates the ratio of PC to PG in the phospholipid used in each fat emulsion.

As is clear from the results shown in Tables 1 to 4, since the fat emulsions of Examples 1 to 12 contained the phospholipid that contained PC and PG and had a ratio of PC to PG (PC:PG) of 85:15 to 99.7:0.3, the residual rate of PGE1 after storage at 40° C. for seven days was 70% or more (80% or more or 85% or more depending on the conditions). Moreover, the average particle diameter of the fat globules was 300 nm or less, and a variation in the average particle diameter of the fat globules was small immediately after preparation, immediately after heating, and after storage at 40° C. for seven days. Therefore, the fat emulsions of Examples 1 to 12 exhibited excellent stability of active ingredient (PGE1) and excellent emulsion stability.

Regarding the fat emulsion of Comparative Example 1, the residual rate of PGE1 in the fat emulsion after storage at 40° C. for seven days was significantly lower than that of the fat emulsion immediately after preparation. Regarding the fat emulsion of Comparative Example 2, a variation in the average particle diameter of the fat globules immediately after heating and after storage at 40° C. for seven days was larger than that of the fat globules immediately after preparation. Moreover, the average particle diameter of the fat globules immediately after heating and after storage at 40° C. for seven days was significantly larger than that of the fat globules immediately after preparation, and separation of the preparation was observed. Regarding the fat emulsion of Comparative Example 3, the particle diameter of the fat globules increased immediately after heating at a pH of 5.0 and 5.5, and the residual rate of PGE1 after storage at 40° C. for seven days decreased at a pH of 6.0. Specifically, since the ratio of PC to PG (PC:PG) in the phospholipid was outside the range of 85:15 to 99.7:0.3 in the fat emulsions of Comparative Examples 1 to 3 and 5, the stability of the active ingredient (PGE1) and/or the emulsion stability deteriorated.

In Comparative Example 4 in which PS was used instead of PG, the emulsion stability was maintained immediately after heating and after storage at 40° C. for seven days. However, the residual rate of PGE1 after storage at 40° C. for seven days was significantly low. In Comparative Example 7 in which PA was used instead of PG, the emulsion stability was maintained immediately after heating and after storage at 40° C. for seven days. However, the residual rate of PGE1 after storage at 40° C. for seven days was significantly low. Specifically, when using PS or PA instead of PG, the emulsion stability was maintained, but PGE1 disappeared rapidly. In Comparative Example 6, the emulsion stability increased by incorporating PE in the phospholipid. However, PGE1 disappeared rapidly as compared with Comparative Examples 1 and 3.

2.21. Results after Storage at 20° C. for Two Months

The fat emulsions (pH: 5.5) of Examples 1 and 7 and Comparative Example 1 were stored at 20° C. for two months. Tables 5 and 6 show the PGE1 residual rate and the average particle diameter after storage. The PGE1 residual rate after storage at 20° C. for two months was calculated using the expression (1).

As is clear from the results shown in Tables 5 and 6, the fat emulsion of Example 1 had an active ingredient (PGE1) stability higher than that of the fat emulsion of Comparative Example 1 even after storage at 20° C. for two months.

TABLE 5

| | Oleic acid (%) | PC:PG | pH | Immediately after preparation PGE1 (microgram/ml) (a) | Immediately after heating PGE1 (microgram/ml) (b) | Immediately after heating PGE1 residual rate (%) (b/a) | After storage at 20° C. for 2 months PGE1 (microgram/ml) (c) | After storage at 20° C. for 2 months PGE1 residual rate (%) (c/b) |
|---|---|---|---|---|---|---|---|---|
| Example 1 | 0 | 98:2 | 5.5 | 5.69 | 5.37 | 94.3 | 4.97 | 92.5 |
| Example 7 | 0 | 98:2 | 5.5 | 6.64 | 6.13 | 92.3 | 5.59 | 91.1 |
| Comparative Example 1 | 0.133 | 100:0 | 5.5 | 7.20 | 6.32 | 87.8 | 4.36 | 69.1 |

TABLE 6

| | pH | Immediately after preparation Average particle diameter (nm) | Immediately after preparation Standard deviation (nm) | Immediately after heating Average particle diameter (nm) | Immediately after heating Standard deviation (nm) | After storage at 20° C. for 2 months Average particle diameter (nm) | After storage at 20° C. for 2 months Standard deviation (nm) |
|---|---|---|---|---|---|---|---|
| Example 1 | 5.5 | 213 | 32 | 211 | 63 | 211 | 79 |
| Example 7 | 5.5 | 218 | 86 | 219 | 68 | 224 | 36 |
| Comparative Example 1 | 5.5 | 214 | 33 | 219 | 47 | 228 | 67 |

2.22. Results after Storage at 5° C. for Six Months

The fat emulsions (pH: 5.5) of Examples 1 and 7 and Comparative Example 1 were stored at 5° C. for six months. Tables 7 and 8 show the PGE1 residual rate and the average particle diameter after storage. The PGE1 residual rate after storage at 5° C. for six months was calculated using the expression (1).

As is clear from the results shown in Tables 7 and 8, the fat emulsions of Examples 1 and 7 had an active ingredient (PGE1) stability higher than that of the fat emulsion of Comparative Example 1 even after storage at 5° C. for six months.

TABLE 7

| | Oleic acid (%) | PC:PG | pH | Immediately after preparation PGE1 (microgram/ml) (a) | Immediately after heating PGE1 (microgram/ml) (b) | Immediately after heating PGE1 residual rate (%) (b/a) | After storage at 5° C. for 6 months PGE1 (microgram/ml) (c) | After storage at 5° C. for 6 months PGE1 residual rate (%) (c/b) |
|---|---|---|---|---|---|---|---|---|
| Example 1 | 0 | 98:2 | 5.5 | 5.69 | 5.37 | 94.3 | 5.36 | 99.8 |
| Example 7 | 0 | 98:2 | 5.5 | 6.64 | 6.13 | 92.3 | 5.99 | 97.6 |
| Comparative Example 1 | 0.133 | 100:0 | 5.5 | 7.20 | 6.32 | 87.8 | 5.32 | 84.2 |

TABLE 8

| | pH | Immediately after preparation Average particle diameter (nm) | Immediately after preparation Standard deviation (nm) | Immediately after heating Average particle diameter (nm) | Immediately after heating Standard deviation (nm) | After storage at 5° C. for 6 months Average particle diameter (nm) | After storage at 5° C. for 6 months Standard deviation (nm) |
|---|---|---|---|---|---|---|---|
| Example 1 | 5.5 | 213 | 32 | 211 | 63 | 227 | 87 |
| Example 7 | 5.5 | 218 | 86 | 219 | 68 | 236 | 64 |
| Comparative Example 1 | 5.5 | 214 | 33 | 219 | 47 | 231 | 52 |

2.23. Results after Storage at 5° C. for One Year

The fat emulsions (pH: 5.5) of Examples 1 and 7 and Comparative Example 1 were stored at 5° C. for one year. Tables 9 and 10 show the PGE1 residual rate and the average particle diameter after storage. The PGE1 residual rate after storage at 5° C. for one year was calculated using the expression (1).

As is clear from the results shown in Tables 9 and 10, the fat emulsions of Examples 1 and 7 had an active ingredient (PGE1) stability higher than that of the fat emulsion of Comparative Example 1 even after storage at 5° C. for one year.

TABLE 9

| | Oleic acid (%) | PC:PG | pH | Immediately after preparation PGE1 (microgram/ml) (a) | Immediately after heating PGE1 (microgram/ml) (b) | PGE1 residual rate (%) (b/a) | After storage at 5° C. for 1 year PGE1 (microgram/ml) (c) | PGE1 residual rate (%) (c/b) |
|---|---|---|---|---|---|---|---|---|
| Example 1 | 0 | 98:2 | 5.5 | 5.69 | 5.37 | 94.3 | 5.13 | 95.6 |
| Example 7 | 0 | 98:2 | 5.5 | 6.64 | 6.13 | 92.3 | 5.60 | 91.4 |
| Comparative Example 1 | 0.133 | 100:0 | 5.5 | 7.20 | 6.32 | 87.8 | 4.71 | 74.5 |

TABLE 10

| | pH | Immediately after preparation Average particle diameter (nm) | Standard deviation (nm) | Immediately after heating Average particle diameter (nm) | Standard deviation (nm) | After storage at 5° C. for 1 year Average particle diameter (nm) | Standard deviation (nm) |
|---|---|---|---|---|---|---|---|
| Example 1 | 5.5 | 213 | 32 | 211 | 63 | 205 | 78 |
| Example 7 | 5.5 | 218 | 86 | 219 | 68 | 218 | 74 |
| Comparative Example 1 | 5.5 | 214 | 33 | 219 | 47 | 211 | 65 |

The invention claimed is:

1. A fat emulsion comprising:
   a prostaglandin as an active ingredient, the fat emulsion including a phospholipid that includes phosphatidylcholine (PC) derived from egg-yolk lecithin and phosphatidylglycerol (PG) and has a ratio of PC to PG (PC:PG) in the range of 95:5 to 99.7:0.3,
   wherein the fat emulsion has an average particle diameter of 300 nm or less.

2. The fat emulsion according to claim 1, wherein the ratio of PC to PG (PC:PG) is 97:3 to 99.7:0.3.

3. The fat emulsion according to claim 1, wherein the fat emulsion substantially does not comprise phosphatidylethanolamine (PE).

4. The fat emulsion according to claim 1, wherein the PG comprises a linear saturated or unsaturated fatty acid residue having 12 to 18 carbon atoms.

5. The fat emulsion according to claim 1, wherein the PG is derived from egg yolk.

6. The fat emulsion according to claim 1, wherein the fat emulsion substantially does not comprise a free higher fatty acid or its salt.

7. The fat emulsion according to claim 1, wherein the fat emulsion substantially does not comprise free oleic acid.

8. The fat emulsion according to claim 1, wherein the fat emulsion comprises a free higher fatty acid or its salt in an amount of 0.15 parts or less by mass with respect to 1 part by mass of the phospholipid.

9. The fat emulsion according to claim 8, wherein the free higher fatty acid is free oleic acid.

10. The fat emulsion according to claim 1, wherein the total content of the PC and the PG in the phospholipid is 95% or more.

11. The fat emulsion according to claim 1, wherein the prostaglandin is prostaglandin E1 or its derivative.

12. The fat emulsion according to claim 11, wherein the prostaglandin is prostaglandin E1, and the fat emulsion having an average particle diameter of 300 nm or less and a prostaglandin E1 residual rate after storage at 40° C. for seven days of 70% or more.

13. The fat emulsion according to claim 11, wherein the prostaglandin is prostaglandin E1, and the fat emulsion having an average particle diameter of 300 nm or less and a prostaglandin E1 residual rate after storage at 20° C. for two months of 80% or more.

14. The fat emulsion according to claim 11, wherein the prostaglandin is prostaglandin E1, and the fat emulsion having an average particle diameter of 300 nm or less and a prostaglandin E1 residual rate after storage at 5° C. for one year of 80% or more.

15. A method for treatment of disorder involving prostaglandin, comprising administering a fat emulsion according to claim 1 to a human or a mammal other than a human by a parenteral administration route.

16. The method for treatment of disorder involving prostaglandin according to claim 15, wherein the parenteral administration route is an intravenous injection.

17. A method of producing a fat emulsion according to claim 1, comprising preparing a fat emulsion that comprises a prostaglandin as an active ingredient comprising a phospholipid that comprises phosphatidylcholine (PC) and phosphatidylglycerol (PG) and has a ratio of PC to PG (PC:PG) of 95:5 to 99.7:0.3.

18. The method of producing a fat emulsion according to claim 17, wherein the ratio of PC to PG (PC:PG) is 97:3 to 99.7:0.3.

19. A method of stabilizing a prostaglandin comprising:
   emulsifying a mixture containing a phospholipid, an oil base, and the prostaglandin as an active ingredient to prepare a fat emulsion,
   wherein the phospholipid includes phosphatidylcholine (PC) derived from egg-yolk lecithin and phosphatidylglycerol (PG) in a ratio of PC to PG (PC:PG) in a range of 95:5 to 99.7:0.3,
   wherein the fat emulsion substantially does not comprise phosphatidylethanolamine (PE); and
   the fat emulsion having an average particle diameter of 300 nm or less.

20. The method of stabilizing a prostaglandin according to claim 19, wherein the ratio of PC to PG (PC:PG) is 97:3 to 99.7:0.3.

21. A fat emulsion comprising:

a prostaglandin as an active ingredient;

a phospholipid that includes phosphatidylcholine (PC) derived from egg-yolk lecithin and phosphatidylglycerol (PG) and has a ratio of PC to PG (PC:PG) of 95:5 to 99.7:03, wherein the fat emulsion substantially does not comprise either phosphatidylethanolamine (PE) or free oleic acid, and the fat emulsion has an average particle diameter of 300 nm or less.

22. The fat emulsion comprising a phospholipid according to claim 21, wherein the ratio of PC to PG (PC:PG) is 97:3 to 99.7:0.3.

* * * * *